United States Patent [19]

Malin et al.

[11] Patent Number: 5,735,587
[45] Date of Patent: Apr. 7, 1998

[54] CLIMATIC CABINET, TURNTABLE AND USE OF THE TURNTABLE

[75] Inventors: Cosmas Malin, Mauren; Harry Sawatzki, Schaan, both of Liechtenstein; Jurg Gentsch, Oberwil, Switzerland; Gunter Helwig, Hanau, Germany

[73] Assignees: Liconic AG, Fürstentum, Liechtenstein; Heraeus Instruments GmbH, Hanau, Germany

[21] Appl. No.: 597,894

[22] Filed: Feb. 5, 1996

[30] Foreign Application Priority Data

Feb. 6, 1995 [CH] Switzerland ............... 00328/95
Sep. 4, 1995 [EP] European Pat. Off. ........ 95113833

[51] Int. Cl.⁶ .................................................. A47F 3/11
[52] U.S. Cl. .................. 312/305; 312/97.1; 312/287; 312/319.7; 108/21; 49/210; 49/219; 435/809
[58] Field of Search ................ 312/97.1, 35, 125, 312/135, 139, 212, 266, 287, 249.2, 305, 319.5, 319.7, 319.8; 108/21, 26, 91; 49/210, 211, 219; 435/809, 303.1

[56] References Cited

U.S. PATENT DOCUMENTS

| 629,367 | 7/1899 | Huxford | 312/125 X |
|---|---|---|---|
| 850,515 | 4/1907 | Boye | 312/72 |
| 2,532,491 | 12/1950 | Frueh | 49/219 |
| 2,606,664 | 8/1952 | Messick | 108/21 |
| 2,628,722 | 2/1953 | Walsh | 108/21 |
| 3,383,798 | 5/1968 | Day | 49/219 |
| 4,250,266 | 2/1981 | Wade | 435/809 X |
| 4,871,676 | 10/1989 | Yamada | |
| 4,930,256 | 6/1990 | Kawanishi et al. | 49/209 |
| 5,470,744 | 11/1995 | Astle | 435/809 X |
| 5,525,512 | 6/1996 | Pieler et al. | 435/809 X |

FOREIGN PATENT DOCUMENTS

| 123695 | 3/1947 | Australia | 312/305 |
|---|---|---|---|
| 531690 | 10/1956 | Canada | 312/97.1 |
| 0 293 782 B1 | 5/1988 | European Pat. Off. | |
| 658274 | 3/1938 | Germany | 312/135 |
| 3610231 | 10/1987 | Germany | 312/305 |
| 1260495 | 9/1986 | U.S.S.R. | 49/210 |

Primary Examiner—Peter R. Brown
Assistant Examiner—Hanh V. Tran
Attorney, Agent, or Firm—Browdy and Neimark

[57] ABSTRACT

A climate cabinet, turntable and use of the turntable. The climatic cabinet (1) can be loaded automatically and manually and has a conventional door (3) and a controllable door (2) as well as a turntable (4) which is connected via a releasable coupling (9) disposed in the interior of the climatic cabinet (1) with a positioning drive (5) and is seated on the floor of the climatic cabinet (1). The controllable door (2) is movably seated on two guide systems (6, 7) perpendicularly and parallel with the loading side (21). The positioning drive (5) is controllable by a higher system or by a user. The turntable (4) has a support shaft (45), tray disks (41) and spacer sleeves as well as spacer tubelets (47, 46) for spacing the tray disks apart, also positioning elements (51) for receiving storage pieces (50). The turntable (41) is suitable for use in a device, for example a climatic cabinet (1), or outside of this device.

9 Claims, 4 Drawing Sheets

CLIMATIC CABINET, TURNTABLE AND USE OF THE TURNTABLE

FILED OF THE INVENTION

The invention relates to a climatic cabinet which can be automatically loaded by a higher system, a turntable for receiving a plurality of storage pieces on at least two tray disks disposed concentrically above each other on a support shaft, and to the use of the turntable in an appliance, for example a climatic cabinet, for treating the storage pieces or their content.

BACKGROUND OF THE INVENTION

Climatic cabinets are used for the creation of defined climatic conditions. Very high demands are made on the homogeneity of the temperature distribution in the interior of the climatic cabinet as well as the thermal insulation of the climatic cabinet, particularly in applications where extreme humidity of the air must be assured. Often such climatic cabinets additionally have double walls with a space between them, in which a temperature-regulating medium (water, air) is present. This requires large wall thicknesses of several centimeters. In uses with automatic loading, access to the climatic cabinet is not only automatic, but often also manual by the user. Particular attention must be paid to the restricted space conditions, on the one hand because of automatic loading provided, mainly by robots and, on the other hand, because of the desire for optimal use of the space. Furthermore, the cleanliness of the interior of the climatic cabinet and the flexible spatial division thereof is of great importance.

An incubator with a rotatable dish storage and an auxiliary door is described by way of example in European Patent Publication EP 0 293 782 B1. This arrangement is not suitable for applications with increased climatic demands, because the auxiliary door provided does not permit the trouble-free bridging of large wall thicknesses. The auxiliary door furthermore is integrated into the service door, which makes simultaneous access by robots and users impossible. The removal of the dish storage is difficult, since the rotational shaft of the dish storage extends past the upper wall of the incubator. Furthermore, the arrangement of the dish storage and the drive mechanism require the placement of the drive mechanism outside the interior of the climatic cabinet, which makes its use difficult in applications where price is a consideration. The structure of the dish storage furthermore is not very stable and does not permit great precision, exact positioning of the shells and only low acceleration.

OBJECT AND SUMMARY OF THE INVENTION

It is therefore a first object of the invention to provide a climatic cabinet which, on the one hand, avoids the disadvantages of the various known devices and, on the other hand, assures the satisfactory capability for loading by means of robotic systems.

A second object of the invention lies in proposing a turntable capable of receiving storage pieces and suitable for use inside as well as outside of a device for treating the storage pieces or their contents.

A third object of the invention lies in disclosing the use of such a turntable.

The first object is attained in connection with a climatic cabinet of the type mentioned at the outset by the features of the characterizing part of claim 1. Preferred further developments and advantageous exemplary embodiments of the climatic cabinet in accordance with the invention are defined in dependent claims 2 to 12.

The second object is attained in a turntable of the type mentioned at the outset by means of the characteristics of claim 13. Preferred exemplary embodiments of the turntable in accordance with the invention are described in dependent claims 14 to 18.

The third object of the invention is contained in claim 19. A special use of the turntable is defined in dependent claim 20.

Thus the novel climatic cabinet has the following features:

- it includes a conventional door on the user side and a controllable door on the loading side;
- the controllable door is seated on one side on a first guidance system so it is movable perpendicularly to the loading side and on the other side on a second guidance system so it is movable parallel with the loading side;
- the turntable is supported on its bottom by means of a bearing;
- the turntable is constructed of tray disks and spacer sleeves;
- positioning elements are provided on the tray disks, constructed on the surface of the tray disks;
- the connection between the turntable and the positioning device is disposed in the interior of the climatic cabinet; and
- the positioning drive can be controlled by the user as well as by the higher system.

The advantages of the invention lie in that the novel climatic cabinet

- has an optimal arrangement of the user and loading doors for robotic applications;
- permits the bridging of great wall thicknesses with a minimal disturbance of the insulation or the temperature-regulating medium;
- precise positioning is possible because of the great stability of the turntable;
- permits a defined position of objects because of the advantageous design of the tray disks and positioning elements;
- assures maximum use of the space on the loading side;
- makes possible the unhampered movement of the loading robot independently of the door position because of the minimum space requirement when the door is opened;
- allows easy removal of the turntable for maintenance work;
- assures easy and secure access for the user;
- assures optimal use of the space in the interior of the climatic cabinet;
- is constructed in such a way that the turntable structure can always be adapted to new requirements; and
- because of the stable structure of the turntable, rapid acceleration, such as required with shaking movements, is made possible.

The advantages of the novel turntable ensue from the respective advantageous properties of the climatic cabinet. It is particularly advantageous that the turntable is usable as a storage device as well as for use in an installation such as a climatic cabinet.

The invention will be described below by means of several exemplary embodiments represented in the drawing figures.

BRIEF DESCRIPTION OF THE DRAWINGS

FIG. 6b is a vertical partial section of a portion of the detail of the tray disk shown in FIG. 6a;

FIG. 7b is a vertical partial section of a portion of the tray disk shown in FIG. 7a.

DETAILED DESCRIPTION OF THE PREFERRED EMBODIMENTS

Figure 1:
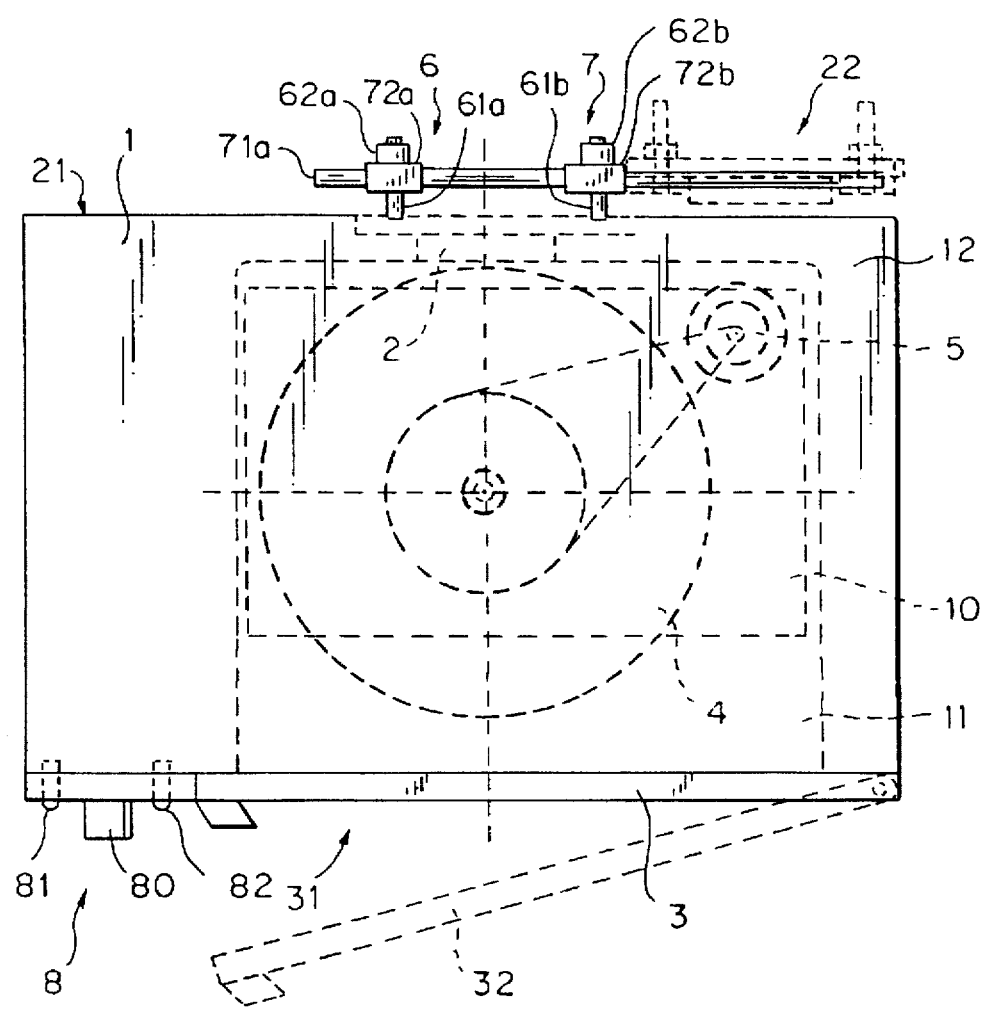
FIG. 1 shows a climatic cabinet in accordance with the invention with a first exemplary embodiment of the controllable door, wherein the positioning drive is located in the work chamber.

The top view of a climatic cabinet 1 with a controllable door 2 on a loading side 21, a conventional door 3 on a user side 31 and a work chamber 11 is shown in FIG. 1. A turntable, hereinafter called turntable structure 4, is provided in the work chamber 11 and is rotated or positioned by means of a positioning drive 5. The turntable structure 4 and the positioning drive 5 are disposed on a plate 10. A wall 12 separates the work chamber 11 from the exterior wall of the climatic cabinet 1. A position selector 80 for semi-automatic positioning of the turntable structure 4 is also disposed on the user side 31. The reference numeral 32 identifies the opened conventional door 3, the reference numeral 22 the controllable door 2 in the completely opened state.

The controllable door 2 is fastened on a first linear guide system 6, which moves the controllable door 2 perpendicularly in respect to the loading side 21. In this case the first linear guide system consists of lift rails 61a, 61b and lift bushings 62a, 62b. The controllable door 2 can perform a lifting motion perpendicularly in respect to the loading side 21 by means of the first linear guide system 6. The first linear guide system 6 itself is fastened on a second linear guide system 7 extending parallel with the loading side 21. The controllable door 2 can be moved parallel with the loading side 21 on the second linear guide system 7 by means of slide bushings 72a, 72b moving on at least one slide rail 71a. The second linear guide system 7 is fastened on the loading side 21 of the climatic cabinet 1. By means of the above arrangement it is possible to bridge large walls 12 or to realize groat wall thicknesses of the controllable door 2 without having to settle for great displacement of the controllable door 2 or large door gaps between the controllable door 2 and the wall 12.

Position selector elements are identified by 8 which make it possible for the user to gain manual access to the turntable structure 4. The position selector 80 is designed in such a way that it allows spatially correct positioning of the turntable structure 4. In the process, a user can determine by means of a first signal lamp 81 or a second signal lamp 82 when the turntable structure 4 is positioned and manual access is possible.

Figure 2:
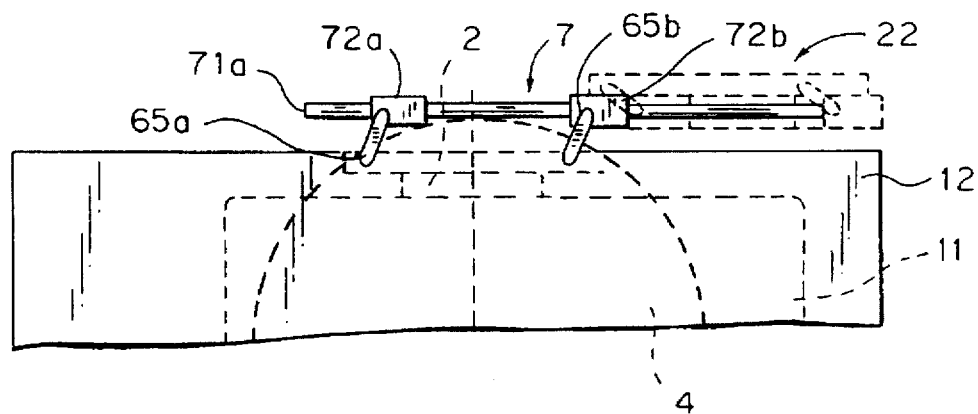
FIG. 2 shows a further climatic cabinet with a second exemplary embodiment of the controllable door in a top view.

A second exemplary embodiment of the controllable door 2 is represented in FIG. 2. In this exemplary embodiment the controllable door 2 is tilted out of the wall 12 by means of tilt levers 65a, 65b and is displaced along the slide rail 71a by means of the slide bushings 72. It is possible to control the tilt levers 65a, 65b by means of a cam plate, not shown, for example.

Figure 3A:
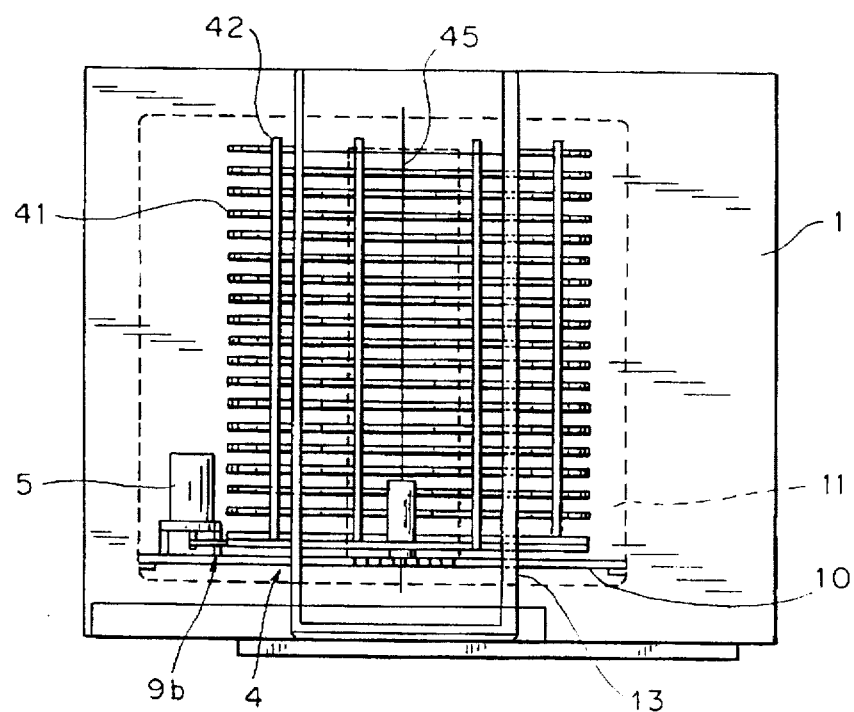
FIG. 3a is a lateral view of the climatic cabinet with the positioning drive located in the work chamber as shown in FIG. 1.

A lateral view of the loading side 21 of the climatic cabinet 1 is represented in FIG. 3a. The turntable structure 4 and the positioning drive 5 are disposed on a plate 10, the seating device for the turntable structure 4 being identified by 13. A connecting point 9b between the turntable structure 4 and the positioning drive 5 is located inside the work chamber 11 and—viewed in a plan view—outside the area of the turntable structure 4. Because the positioning drive 5 is disposed on the plate 10 together with the turntable structure 4 it is possible in a simple manner to remove the entire turntable structure 4 from the work chamber 11 together with the plate 10. The turntable structure is otherwise designed in such a way that it is also suited for use outside of the climatic cabinet 1.

Figure 3B:
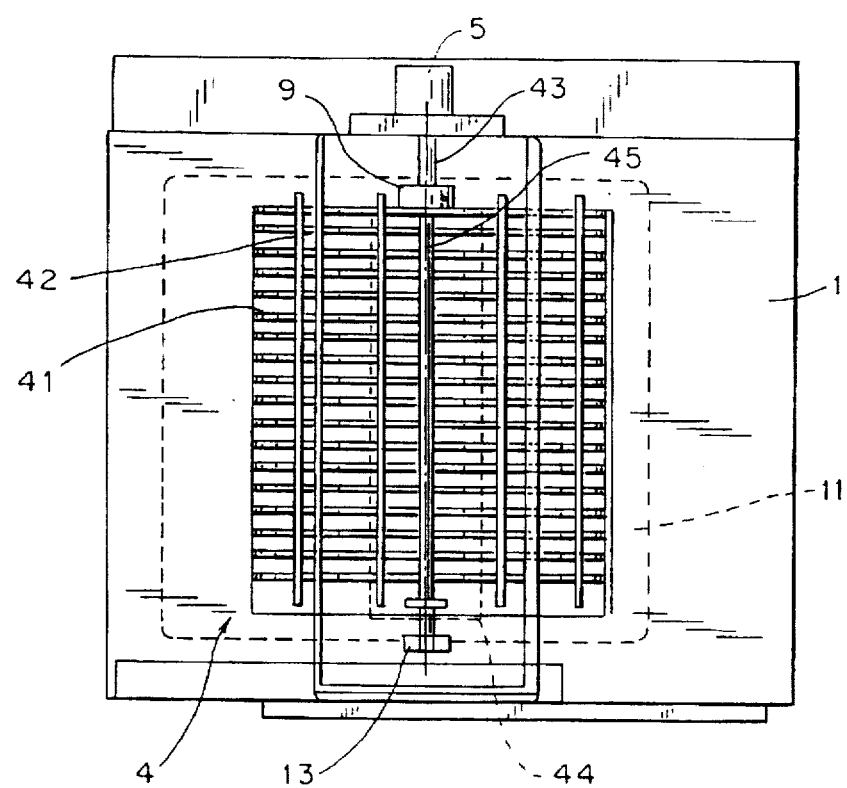
FIG. 3b is a lateral view of a climatic cabinet in accordance with the invention with a positioning drive located outside of the work chamber.

A lateral view of the climatic cabinet 1 from the direction of the loading side 21 is also shown in FIG. 3b. The turntable structure 4 rests on the floor of the work chamber 11, wherein the seating is again indicated by 13. An optimal use of the space in the work chamber 11 is possible because of this arrangement. The connection between the turntable structure 4 and the positioning drive 5 is made by a coupling 9. In this exemplary embodiment the positioning drive 5 has the same axis of rotation as the turntable structure 4. A drive shaft 43 of the positioning drive 5, wherein the change in direction is also realized by means of the latter, is connected via the coupling 9 with a support shaft 45 of the turntable structure 4. The coupling 9 is disposed inside the work chamber 11. This permits the simple installation or removal of the turntable structure 4.

The turntable structure 4 is constructed of tray disks 41 located above each other.

Figure 4:
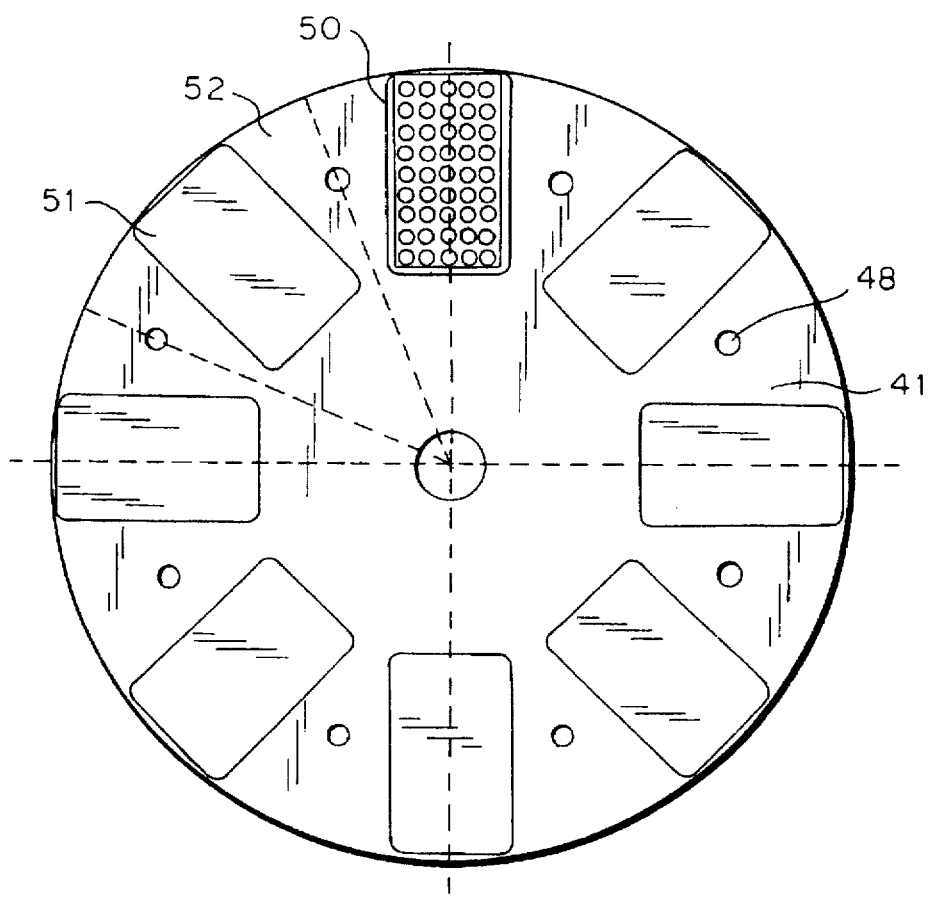
FIG. 4 is a top view of an exemplary embodiment of a tray disk.

FIG. 4 shows an exemplary embodiment of a tray disk 41 in a top view. In addition to a central bore concentric in respect to the support shaft 45, the tray disk 41 has a plurality, at least three support bores 48 in the rim area of the tray disk 41. The tray disk 41 is divided in a star shape into segments 52. The segments 52 are respectively used for receiving a rectangular storage piece 50. The storage piece 50 is maintained by positioning elements 51 on the tray disk 41. In the exemplary embodiment of FIG. 4, the positioning elements 51 are provided in the form of depressions in the shape of the top-view contours of the storage piece 50, cut into the tray disk 41.

Figure 5:
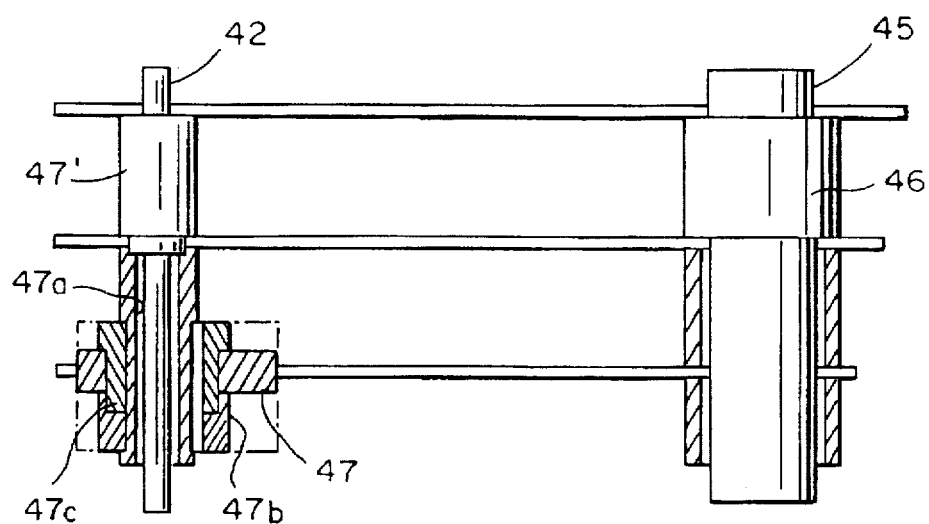
FIG. 5 is a lateral view, partially in section, of an exemplary embodiment of the turntable with spacer sleeves.

FIG. 5 represents a partially sectional view of the turntable structure 4. Beside the support shaft 45, which forms the axis of rotation, the turntable structure 4 has at least three turntable supports 42 extending parallel with the support shaft 45 and perpendicular in respect to the tray disks 41. The support shaft 45 is disposed in the center of rotation of the turntable structure 4. The tray disks 41 are arranged concentrically with the support shaft 45 at defined distances on top of each other. The spaces between the tray disks 41 are formed by spacer sleeves 47. The spacer sleeves 47 comprise and/or external sleeves. They have centering steps and have a longitudinal bore 47a, a centering bore 47b and centering collars 47c. The interior diameter of the center bore 47b is equal to the exterior diameter of the centering collar 47c. The diameter of the support bores 48 in the tray disk 41 is equal to the diameter of the centering bore 47b. The centering collar 47c of each spacer sleeve 47 is guided by the support bore 48 of one tray disk 41. A chain of tray disks 41 and spacer sleeves 47 is formed in this way, in which respectively one tray disk 41, guided by the centering collar 47c, is located between two spacer sleeves 47. In the interior of the chain a bracing rod 42 extends along the longitudinal bores 47a and longitudinally braces the spacer sleeves 47 or the tray disks 41 at both ends of the chain in a manner not shown. A simplified collar 47' is also shown in FIG. 5.

To obtain optimal stability of the turntable structure 4 and a level placement of the tray disks 41, it is advantageous to additionally brace the turntable structure 4 in the center. In the present exemplary embodiment, spacer tubelets 46 are disposed between the tray disks 41. The spacer tubelets 46 have the same length as the spacer sleeves 47 of a respective level and enclose the support shaft 45. The spacer tubelets 46 or the tray disks 41 rest on the underside of the turntable structure 4 on a flange 44, shown in FIG. 3b, which is connected with the support shaft 45. On the top of the turntable structure 4 the spacer tubelets 46 are braced against the flange 44 by means of the coupling 9.

Figure 6A:
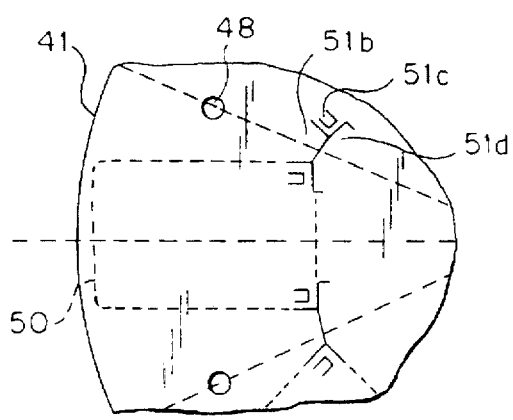
FIG. 6a is a top view of a first exemplary embodiment of a detail of the tray disk.

FIG. 6a shows a section of a detailed representation of an exemplary embodiment of the tray disk 41 of FIG. 4 with specially designed positioning elements 51. In this case they are embodied as tongues 51b to 51d, projecting past the surface of the tray disk 41. In this exemplary embodiment the storage piece 50 is held radially on the inside and outside of its lateral walls by the positioning elements 51c and 51d and tangentially by the positioning elements 51b and 51c.

Figure 6B:
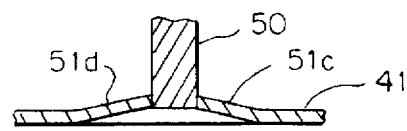

FIG. 6b explains the structure of FIG. 6 in a partial sectional view.

Figure 7A:
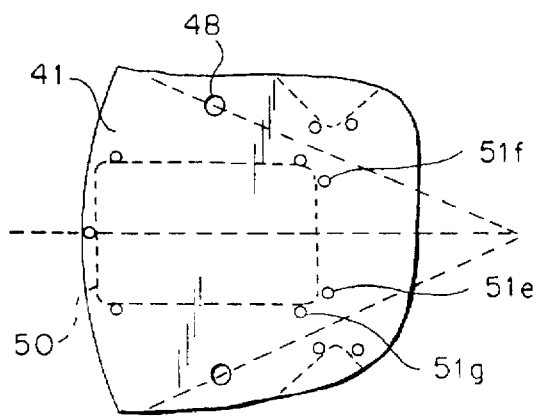
FIG. 7a is a top view of a second exemplary embodiment of the detail of the tray disk.

FIG. 7a represents a variant of the design for holding the storage pieces 50 by means of positioning elements 51. In this exemplary embodiment the positioning elements 51 are pins 51e to 51g which are pressed into the tray disk 41 in such a way that a portion of the pressed-in pins 51e to 51g extends above the surface of the tray disk 41. In this case the pins 51e and 51f are arranged in such a way that they hold the storage piece 50 radially and the pins 51g hold it tangentially on the sidewalls of the storage piece 50.

Figure 7B:
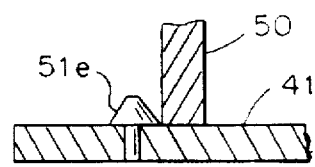

FIG. 7b explains the structure of FIG. 7a in a partial sectional view.

In order to assure the same climatic conditions for all storage pieces 50, independently of their location inside the work chamber 11, the turntable structure 4 performs a continuously rotating movement. In cases where the mixing of a liquid in the storage pieces is required, shaking is generated by intermittent directional change of the rotary movement of the turntable structure 4. By means of a small deviation of the two periods of time for the forward and backward movement, a rotary movement is superimposed on the shaking movement in this case. The operating elements, i.e. the position selector elements 8, can also contain a higher system which allows the user to link the schedule and the contents of the storage pieces 50 in such a way that, for example, the user can determine when and how long the samples to be treated should remain in the climatic cabinet.

What is claimed is:

1. A climatic cabinet including an interior work chamber (11) with access for a user thereto on a user side (31) and with access for an automatic system thereto on a loading side (21), comprising:
    (a) a conventional door (3) accessing the work chamber on the user side;
    (b) a controllable door (2) accessing the work chamber on the loading side, the controllable door being mounted to the cabinet by
    a first guidance system (6) including means for moving the controllable door perpendicularly to the loading side, and by
    a second guidance system (7) including means for moving the controllable door parallel to the loading side;
    (c) a turntable (4) rotatably supported on a bearing (13) disposed on a floor of the work chamber, the turntable further comprising
    a support shaft (45),
    a plurality of tray disks (41), and
    at least three spacer sleeves (47), and wherein
    the support shaft and the spacer sleeves are disposed perpendicularly to the tray disks;
    the tray disks including respective tray surfaces including positioning elements (51) arising therefrom;
    (d) a positioning drive (5);
    means for controlling the positioning drive by both the user and the automatic system; and
    (e) a coupling (9) between the turntable (4) and the positioning drive (5), the coupling being disposed inside the work chamber; wherein
    the first guidance system (6) and the second guidance system (7) each comprise a respective linear guide system, the second guidance system (7) is mounted parallel to the loading side (21) and the first guidance system (6) is disposed on the second guidance system (7).

2. A climatic cabinet including an interior work chamber (11) with access for a user thereto on a user side (31) and with access for an automatic system thereto on a loading side (21), comprising:
    (a) a conventional door (3) accessing the work chamber on the user side;
    (b) a controllable door (2) accessing the work chamber on the loading side, the controllable door being mounted to the cabinet by
    a first guidance system (6) including means for moving the controllable door perpendicularly to the loading side, and by
    a second guidance system (7) including means for moving the controllable door parallel to the loading side;
    (c) a turntable (4) rotatably supported on a bearing (13) disposed on a floor of the work chamber, the turntable further comprising
    a support shaft (45),
    a plurality of tray disks (41), and
    at least three spacer sleeves (47), and wherein
    the support shaft and the spacer sleeves are disposed perpendicularly to the tray disks;
    the tray disks including respective tray surfaces including positioning elements (51) arising therefrom;
    (d) a positioning drive (5);
    means for controlling the positioning drive by both the user and the automatic system; and
    (e) a coupling (9) between the turntable (4) and the positioning drive (5), the coupling and the positioning drive being disposed inside the work chamber.

3. The climatic cabinet in accordance with claim 2, wherein the first guidance system (6) is a rotational guide system and the second guidance system (7) is a linear guide system, wherein the rotational guide system moves the controllable door (2) perpendicularly to the loading side (21) and is arranged on the second linear guide system (7) which is parallel with the loading side (21).

4. The climatic cabinet in accordance with claim 2, wherein the spacer sleeves comprise at least three external spacer sleeves (47), which are disposed in the rim area of the tray disks (41) and have centering steps, and the tray disks (41) are kept together by bracing elements extending parallel with the spacer sleeves (47).

5. The climatic cabinet in accordance with claim 2, characterized in that the positioning elements (51) comprise slits in the tray disk (41) and include tongues (51b to 51d) bent up out of the tray disk surface along the slits.

6. The climatic cabinet in accordance with claim 2, wherein the positioning elements (51) are pins (51e to 51g) pressed perpendicularly into the tray disk (41).

7. The climatic cabinet in accordance with claim 2, comprising means for intermittently controlling the direction of rotation of the turntable (4) provided in the positioning drive (5).

8. The climatic cabinet in accordance with claim 7, wherein the means for intermittently controlling include means such that a rotational movement can be superimposed on a change of rotational direction.

9. The climatic cabinet in accordance with claim 2, wherein comprising a position selector (80) for presetting the desired stop position of the turntable and at least one signal lamp or buzzer for indicating the end of the positioning process.

* * * * *